United States Patent [19]

Schaub et al.

[11] 4,399,126

[45] Aug. 16, 1983

[54] MODULATORS OF THE COMPLEMENT SYSTEM

[75] Inventors: Robert E. Schaub, Upper Saddle River, N.J.; Janis Upeslacis, Pomona; Seymour Bernstein, New City, both of N.Y.

[73] Assignee: American Cyanamid Company, Stamford, Conn.

[21] Appl. No.: 369,047

[22] Filed: Apr. 16, 1982

[51] Int. Cl.³ .................. A61K 31/70; A61K 31/73; C07H 3/06
[52] U.S. Cl. .................................. 424/180; 536/4.1; 536/17.6; 536/118
[58] Field of Search ................. 424/180; 536/4.1, 118, 536/17.6

[56] References Cited

U.S. PATENT DOCUMENTS

| 4,258,034 | 3/1981 | Joseph et al. | 424/180 |
| 4,304,904 | 12/1981 | Nair et al. | 536/4 |
| 4,334,058 | 1/1982 | Nair et al. | 536/8 |
| 4,337,249 | 1/1982 | Conzow et al. | 424/180 |

Primary Examiner—Donald B. Moyer
Assistant Examiner—Ciro Joseph Faraci
Attorney, Agent, or Firm—Anne M. Rosenblum

[57] ABSTRACT

N,N'-Bis[4-[2,3,6,-tri-O-sulfo-4-O-(2,3,4,6-tetra-O-sulfo-α(and β)-D-glucopyranosyl)-α(and β)-D-glucopyranosylthio or sulfinyl or sulfonyl]phenyl]alkyldiamides and alkyldiamines, the cation salts thereof, useful as modulators of the complement system, the intermediates thereof and the process of making such intermediates and end products.

76 Claims, No Drawings

MODULATORS OF THE COMPLEMENT SYSTEM

BACKGROUND OF THE INVENTION

1. Field of the Invention

The present invention relates to novel compounds, N,N'-Bis[4-[2,3,6-tri-O-sulfo-4-O-(2,3,4,6-tetra-O-sulfo-α(and β)-D-glucopyranosyl)-α(and β)-D-glucopyranosylthio or sulfinyl or sulfonyl]phenyl]alkyldiamides and alkyldiamines, the cation salts thereof, to their use as modulators of the complement system of warm-blooded animals, to the intermediates thereof and to the process for the preparation of such intermediates and end products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); John Hopkins Med. J. 128: 57 (1971); Harvey Lect. 66: 75 (1972); N. Engl. J. Med. 287: 452, 489, 545, 592, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976-1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement sysem (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease desseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus. it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis-[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Patent No. 2,254,893 or South African Patent No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819 (1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

The instant invention relates to new compounds, N,N'-bis[4-[2,3,6-tri-O-sulfo-4-O-(2,3,4,6-tetra-O-sulfo-α(and β)-D-glucopyranosyl)-α(and β)-D-glucopyranosylthio or sulfinyl or sulfonyl]phenyl]alkyldiamides and alkyldiamines, and the cation salts thereof, that modulate the complement system, thereby modulating complement activity in body fluids. Moreover, this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

This invention also deals with the novel precursors that act as intermediates in preparing the above-described complement modulating compounds of this invention.

DETAILED DESCRIPTION OF THE INVENTION

In accordance with the present invention, there are provided novel compounds represented by the following generic Formula I:

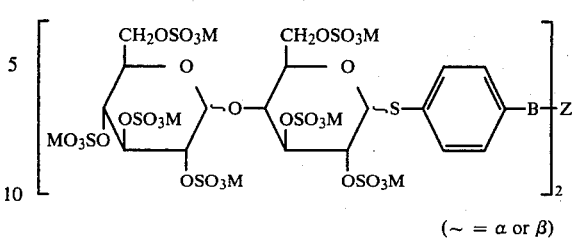

FORMULA I ($\sim$ = α or β)

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); B is selected from the group consisting of —NHCO—, —NHSO$_2$—, —NHCH$_2$— and —NH—; and Z is a straight or branched chain alkylidene group —(CH$_2$)$_m$—, where m is an integer 0–12, inclusive, with the proviso that when m is zero or one, B cannot be —NHSO$_2$—, which compounds are highly active as complement modulators.

Particularly preferred compounds of Formula I which are of major interest as modulators of the complement system are:

tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]propanediamide tetradecasodium N,N'-bis[2,3,6-tri-O-sulfo-4-O-(2,3,4,6-tetra-O-sulfo-α-D-glucopyranosyl)-β-D-glucopyranosylthio]phenyl]butanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]pentanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]hexanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]heptanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide tetradecasodium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]propanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]pentanediamide tetradecatriethylammonium N,N'-bis[4[2,3,6-tri-O-sulfo-4-O-(2,3,4,6-tetra-O-sulfo-α-D-glucopyranosyl)-β-D-gluocopyranosylthio]phenyl]hexanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]heptanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide tetradecatriethylammonium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine.

Other representative compounds of Formula I include the series starting with tetradecasodium N,N'-bis[4-[2,3,6-tri-O-sulfo-4-O-(2,3,4,6-tetra-O-sulfo-α-D-glucopyranosyl)-β-D-glucopyranosylthio[phenyl]ethanediamine, propanediamine, propanedisulfonamide, etc. and the triethyl-ammonium salt derivatives.

This invention further deals with a method of modulating the complement system in a body fluid, such as blood serum, which comprises subjecting body fluid complement to the action of an effective complement modulating amount of a compound of the above Formula I. Body fluids can include blood, plasma, serum, synovial fluid, cerebrospinal fluid, or pathological accumulations of fluid such as pleural effusion, etc. This invention also concerns a method of modulating the complement system in a warm-blooded animal which comprises administering to said warm-blooded animal an effective complement modulating amount of a compound of Formula I.

In addition, this invention is concerned with the precursors in the preparation of the complement modulating compounds of Formula I, shown by the following Formula II:

FORMULA II

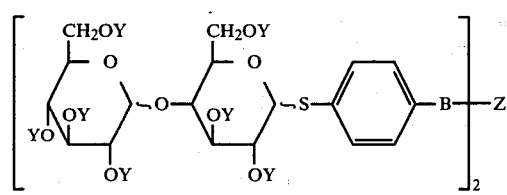

wherein Y is selected from the group consisting of H and COCH$_3$; and B and Z are as described in Formula I.

Specific compounds of Formula II which are of particular interest as intermediates for the production of the compounds of Formula I include the following:

N,N'-bis[4-[2,3,6-tri-O-acetyl-4-O-(2,3,4,6-tetra-O-acetyl-α-D-glucopyranosyl)-β-D-glucopyranosylthio]phenyl]ethanediamide N,N-bis[4-[2,3,6-tri-O-acetyl-4-O-(2,3,4,6-tetra-O-acetyl-α-D-glucopyranosyl)-β-D-glucopyranosylthio]phenyl]propanediamide N,N'-bis[4-[2,3,6-tri-O-acetyl-4-O-(2,3,4,6-tetra-O-acetyl-α-D-glucopyranosyl)-β-D-glucopyranosylthio]phenyl]butanediamide N,N'-bis[4-[2,36-tri-O-acetyl-4-O-(2,3,4,6-tetra-O-acetyl-α-D-glucopyranosyl)-β-D-glucopyranosylthio]phenyl]pentanediamide N,N'-bis[4-[2,3,6-tri-O-acetyl-4-O-(2,3,4,6-tetra-O-acetyl-α-D-glucopyranosyl)-β-D-glucopyranosylthio]phenyl]hexanediamide N,N'-bis[4-[2,3,6-tri-O-acetyl-4-O-(2,3,4,6-tetra-O-acetyl-α-D-glucopyranosyl)-β-D-glucopyranosylthio]phenyl]heptanediamide N,N'-bis[4-[2,3,6-tri-O-acetyl-4-O-(2,3,4,6-tetra-O-acetyl-α-D-glucopyranosyl)-β-D-glucopyranosylthio]phenyl]octanediamide N,N'-bis[4-[2,3,6-tri-O-acetyl-4-O-(2,3,4,6-tetra-O-acetyl-α-D-glucopyranosyl)-β-D-glucopyranosylthio]phenyl]decanediamide N,N'-bis[4-[2,3,6-tri-O-acetyl-4-O-(2,3,4,6-tetra-O-acetyl-α-D-glucopyranosyl)-β-D-glucopyranosylthio]phenyl]tetradecanediamide N,N'-bis[4-[2,3,6-tri-O-acetyl-4-O-(2,3,4,6-tetra-O-acetyl-β-D-glucopyranosyl)-β-D-glucopyranosylthio]phenyl]pentanediamide N,N'-bis[4-[4-O-(α-D-glucopyranosyl)-β-D-glucopyranosylthio]phenyl]ethanediamide N,N'-bis[4-[4-O-(α-D-glucopyranosyl)-β-D-glucopyranosylthio]phenyl]propanediamide N,N'-bis[4-[4-O-(α-D-glucopyranosyl)-β-D-glucopyranosylthio]phenyl]butanediamide N,N'-bis[4-[4-O-(α-D-glucopyranosyl)-β-D-glucopyranosylthio]phenyl]pentanediamide N,N'-bis[4-[4-O-(α-D-glucopyranosyl)-β-D-glucopyranosylthio]phenyl]hexanediamide N,N'-bis[4-[4-O-(α-D-glucopyranosyl)-β-D-glucopyranosylthio]phenyl]heptanediamide N,N'-bis[4-[4-O-(α-D-glucopyranosyl)-β-D-glucopyranosylthio]phenyl]octanediamide N,N'-bis[4-[4-O-(α-D-glucopyranosyl)-β-D-glucopyranosylthio]phenyl]decanediamide N,N'-bis[4-[4-O-(α-D-glucopyranosyl)-β-D-glucopyranosylthio]phenyl]tetradecanediamide N,N'-bis[4-[4-O-(β-D-glucopyranosyl)-β-D-glucopyranosylthio]phenyl]pentanediamide N,N'-bis[4-[4-O-(α-D-glucopyranosyl)-β-D-glucopyranosylthio]phenyl]butanediamine In the above Formulas I and II the sugar molecule is drawn to represent either maltose or cellobiose. This invention is not restricted to these two disaccharides, but instead is intended to include disaccharides consisting of aldohexoses, ketohexoses, aldopentoses and the like as well as oligosaccharides wherein the sugar units are 2–8 consisting of maltotrioses, maltotetraoses, maltopentaoses and the like.

The compounds of Formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example, inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of Formula II may be useful as immuno-enhancing agents or potentiators.

The compounds of this invention may be prepared according to the following flowchart.

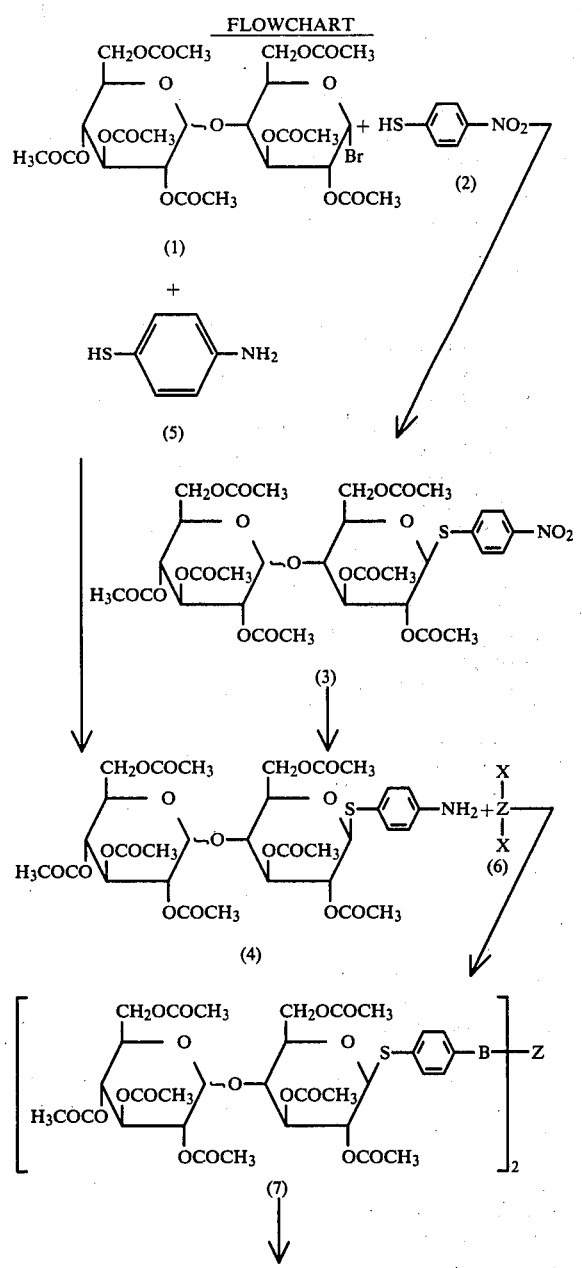

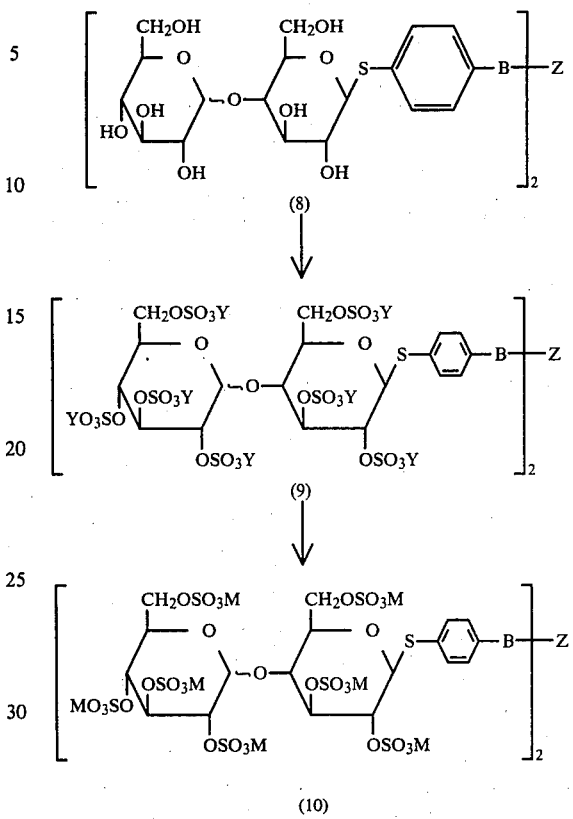

In accordance with the above flowchart, a brominated peracetyl sugar (1) is reacted with a p-nitrothio phenol (2), and sodium hydride in a solvent such as dimethoxyethane under an inert atmosphere for several hours, giving a 4-nitrophenyl 2,3,6-tri-O-acetyl-4-O-(2,3,4,6-tetra-O-acetyl-$\alpha$(or $\beta$)-D-glucopyranosyl)-1-thio-$\alpha$(or $\beta$)-D-glucopyranoside (3) which is then catalytically reduced to the corresponding 4-aminophenyl derivative (4). Alternatively, similar reaction of (1) with p-aminothiophenol (5) produces (4) directly without requiring reduction. The derivative (4) is then treated with an acid chloride (6) where X is, for example, COCl or SO$_2$Cl; Z is —(CH$_2$)$_m$— and m is an integer 0–12 in a solvent such as acetonitrile under an inert atmosphere for several hours giving a N,N'-bis[4-[2,3,6-tri-O-acetyl-4-O-(2,3,4,6-tetra-O-acetyl-$\alpha$(or $\beta$)-D-glucopyranosyl)-$\alpha$(or $\beta$)-D-glucopyranosylthio]phenyl]alkyldiamide (7), where Z is as described above and B is, for example, —NHCO—. The derivative (7) is then reacted with ammonia-saturated methanol at $-5°$ to $+5°$ C. under an inert atmosphere or with sodium in methanol for several hours giving a N,N'-bis[4-[4-O-($\alpha$(or $\beta$)-D-glucopyranosyl)-$\alpha$(or $\beta$)-D-glucopyranosylthio]phenyl]alkyldiamide (8) where B and Z are as described above. The derivative (7) may also be reduced with diborane in dry tetrahydrofuran under an inert atmosphere at $-5°$ to $+5°$ C., giving the derivative (8) where Z is as described above and B is —NHCH$_2$—. Derivative (8) is then reacted with triethylamine-sulfur trioxide complex in N,N-dimethylacetamide, under an inert atmosphere at 60°–65° C. for several hours, giving the tetradecatriethylammonium derivative (9), where Y is NH$^+$(C$_2$H$_5$)$_3$ which is then, if desired, reacted with a cation-containing compound wherein the salt forming moiety is selected from the group consisting of alkali metal, alkaline earth metal, aluminum, ammonia and substituted ammonia selected from the group consisting of piperidine, pyrazine, alkanolamine ($C_2$–$C_6$) and cycloalkylamine ($C_3$–$C_6$), and thereafter precipitated in ethanol, giving the end product (10) of this invention.

It is generally preferred that the respective product of each process step, described hereinabove, is separated and/or isolated prior to its use as starting material for subsequent steps. Separation and isolation can be effected by any suitable purification procedure such as, evaporation, crystallization, column chromatography, thin-layer chromatography, distillation, etc. Also it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salt forming moieties of the present invention which are pharmaceutically acceptable include the alkali metals (e.g., sodium, potassium, etc.); alkaline earth metals (e.g., calcium, etc.); aluminum; ammonia; and substituted ammonia selected from the group consisting of trialkylamine ($C_1$–$C_6$), piperidine, pyrazine, alkanolamine ($C_2$–$C_6$) and cycloalkylamine ($C_3$–$C_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

4-Aminophenyl 2,3,6-tri-O-acetyl-4-O-(2,3,4,6-tetra-O-acetyl-α-D-glucopyranosyl)-1-thio-β-D-glucopyranoside A solution of 5.13 g of 4-aminothiophenol in 50 ml of dry dimethoxyethane was added dropwise, at a rapid rate, to a stirred mixture of 1.8 g of 50% sodium hydride in oil, under argon. The mixture was stirred for 3–4 hours, then a solution of 25.8 g of acetobromo-α-D-maltose in 75 ml of dimethoxyethane was added dropwise, at a fast rate. The mixture was stirred for 18 hours, filtered and the filtrate concentrated to a brown oil. This oil was purified by dry column chromatography on 1300 g of silica gel, using ethyl acetate-hexane (1:1) as eluant. Crystallization of the residual oil from ether gave 13.8 g of the desired product as white crystals, m.p. 147°–148° C.

EXAMPLE 2

4-Nitrophenyl 2,3,6-tri-O-acetyl-4-O-(2,3,4,6-tetra-O-acetyl-α-D-glucopyranosyl)-1-thio-β-D-glucopyranoside A 20.2 g sample of 50% sodium hydride in oil dispersion was washed free of oil with hexane and suspended in 300 ml of dry dimethoxyethane under argon. To the stirred suspension was added dropwise a solution of 65 g of 4-nitrothiophenol in 130 ml of dimethoxyethane. After the addition of 4-nitrothiophenol, stirring was continued for one hour, then a solution of 235 g of bromoheptaacetylmaltose in 800 ml of dry dimethoxyethane was added dropwise during one-half hour. After 2 hours of stirring at room temperature, excess sodium hydride was destroyed by the addition of 10 ml of acetic acid. Dimethoxyethane was evaporated under reduced pressure and the residue was partitioned between one liter of methylene chloride and 500 ml of water. The layers were separated, the water layer was extracted once more with 500 ml of methylene chloride, the organic layers were combined, washed with brine, dried with magnesium sulfate, and the solution was passed through a pad of magnesium silicate. The pad was washed thoroughly with methylene chloride and ether, the solvents were evaporated, and the residual orange foam was crystallized from 2 liters of methanol to yield 179.5 g of faintly yellow crystals, m.p. 163°–165° C.

EXAMPLE 3

4-Aminophenyl 2,3,6-tri-O-acetyl-4-O-(2,3,4,6-tetra-O-acetyl-α-D-glucopyranosyl)-1-thio-β-D-glucuopyranoside To 91.3 g of 4-nitrophenyl 2,3,6-tri-O-acetyl-4-O-(2,3,4,6-tetra-O-acetyl-α-D-glucopyranosyl)-1-thio-β-D-glucopyranoside suspended in 200 ml of acetic acid was added 10 g of 10% palladium-on-charcoal catalyst in a Parr hydrogenation bottle, and this was hydrogenated on a Parr hydrogenator for 17 hours. The catalyst was filtered from the solution through diatomaceous earth and washed thoroughly with methanol. The solvents were evaporated in vacuo. The residue was dissolved in one liter of toluene and again evaporated. The residue was dissolved in methylene chloride and passed through a pad of magnesium silicate and the volume of the solution was adjusted to about 300 ml. To this was added 1.5 liters of ether and 5 g of activated charcoal, the solution was boiled for 3 minutes, the charcoal was filtered off and the solvents were again evaporated. The yellow foam was crystallized from 1.5 liters of ether to yield 69.6 g of light yellow crystals, isolated in three crops, m.p. 145°–148° C.

EXAMPLE 4

N,N'-Bis[4-[2,3,6-tri-O-acetyl-4-O-(2,3,4,6-tetra-O-acetyl-α-D-glucopyranosyl)-β-D-glucopyranosylthio]phenyl]octanediamide To a stirred solution of 25 g of 4-aminophenyl 2,3,6-tri-O-acetyl-4-O-(2,3,4,6-tetra-O-acetyl-α-D-glucopyranosyl)-1-thio-β-D-glucopyranoside in 250 ml of a dry mixture of pyridine-acetonitrile (1:1) was added a solution of 3.55 g of suberoyl chloride in 10 ml of acetonitrile. This mixture was allowed to stand, under argon, for 18 hours. An additional 0.2 ml of suberoyl chloride was added, the solution was allowed to stand for an additional 18 hours and was then poured into 2 liters of water. After stirring for 15 minutes, the oil was separated and extracted into 500 ml of dichloromethane. The extract was washed twice with 500 ml portions of 0.5 N hydrochloric acid, then with saturated aqueous sodium chloride solution, dried and taken to dryness, giving 28 g of the desired product as a white foam.

EXAMPLES 5–13

Treatment of 4-aminophenyl 2,3,6-tri-O-acetyl-4-O-(2,3,4,6-tetra-O-acetyl-α-D-glucopyranosyl)-1-thio-β-D-glucopyranoside or other appropriate disaccharides, as well as the -1-oxy- derivatives of this and other appropriate disaccharides, with other acid chlorides according to the procedure of Example 4, gave the products of Examples 5–13 as shown in the following Table I.

TABLE I

| Example | Acid Chloride | Product |
|---|---|---|
| 5 | Succinyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]butanediamide |
| 6 | Glutaryl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]pentanediamide |
| 7 | Adipoyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]hexanediamide |
| 8 | Pimeloyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]heptanediamide |
| 9 | Sebacyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]decanediamide |
| 10 | Malonyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]propanediamide |
| 11 | Tetradecanedioyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]tetradecanediamide |
| 12 | Oxalyl chloride | N,N'—Bis[4-[2,3,6-tri-O—acetyl-4-O—(2,3,4,6-tetra-O—acetyl-α-D-glucopyranosyl)-β-D-glucopyranosylthio]phenyl]ethanediamide |
| 13 | Glutaryl chloride | N,N'—Bis[4-[2,3,6-tri-O—acetyl-4-O—(2,3,4,6-tetra-O—acetyl-β-D-glucopyranosyl)-β-D-glucopyranosylthio]phenyl]pentanediamide |

EXAMPLE 14

N,N'-Bis[4-[4-O-(α-D-glucopyranosyl)-β-D-glucopyranosylthio]phenyl]octanediamide A 28.4 g portion of N,N'-bis[4-[2,3,6-tri-O-acetyl-4-O-(2,3,4,6-tetra-O-acetyl-α-D-glucopyranosyl)-β-D-glucopyranosylthio]phenyl]octanediamide was dissolved in a 0° C. solution of 500 ml of methanol saturated with ammonia. The solution was allowed to stand at 0° C., under an inert atmosphere, for 18 hours, then was warmed to ambient temperature and evaporated. The residue was triturated with 200 ml of absolute ethanol, filtered, washed in sequence with absolute ethanol, acetonitrile, then ether and dried in vacuo at 40° C., giving 12.1 g of the desired intermediate as an amorphous solid.

EXAMPLES 15–23

Treatment of the products of Examples 5–13 by the procedure of Example 14 resulted in the intermediate products of Examples 15–23, given in Table II.

TABLE II

| Example | Starting Material (Example) | Product |
|---|---|---|
| 15 | 5 | N,N'—Bis[4-[4-O—(α-D-glucopyranosyl)-β-D-glucopyranosylthio]phenyl]butanediamide |
| 16 | 6 | N,N'—Bis[4-[4-O—(α-D-glucopyranosyl)-β-D-glucopyranosylthio]phenyl]pentanediamide |
| 17 | 7 | N,N'—Bis[4-[4-O—(α-D-glucopyranosyl)-β-D-glucopyranosylthio]phenyl]hexanediamide |
| 18 | 8 | N,N'—Bis[4-[4-O—(α-D-glucopyranosyl)-β-D-glucopyranosylthio]phenyl]heptanediamide |
| 19 | 9 | N,N'—Bis[4-[4-O—(α-D-glucopyranosyl)-β-D-glucopyranosylthio]phenyl]decanediamide |
| 20 | 10 | N,N'—Bis[4-[4-O—(α-D-glucopyranosyl)-β-D-glucopyranosylthio]phenyl]propanediamide |
| 21 | 11 | N,N'—Bis[4-[4-O—(α-D-glucopyranosyl)-β-D-glucopyranosylthio]phenyl]tetradecanediamide |
| 22 | 12 | N,N'—Bis[4-[4-O—(α-D-glucopyranosyl)-β-D-glucopyranosylthio]phenyl]ethanediamide |
| 23 | 13 | N,N'—Bis[4-[4-O—(β-D-glucopyranosyl)-β-D-glucopyranosylthio]phenyl]pentanediamide |

EXAMPLE 24

N,N'-Bis[4-[4-O-(α-D-glucopyranosyl)-β-D-glucopyranosylthio]phenyl]butanediamine A 9.2 g portion of N,N'-bis[4-[2,3,6-tri-O-acetyl-4-O-(2,3,4,6-tetra-O-acetyl-α-D-glucopyranosyl)-β-D-glucopyranosylthio]phenyl]butanediamide in 30 ml of dry tetrahydrofuran was cooled in an ice bath. To this was added with magnetic stirring dropwise 210 ml of 1 M solution of diborane in tetrahydrofuran. The solution was allowed to come to room temperature overnight and the excess diborane was decomposed by the addition of methanol. The white solid which separated during the reaction was collected by filtration and was suspended in 500 ml of methanol saturated with ammonia at 0° C. The mixture was stirred overnight and the solid gradually dissolved as the temperature rose to room temperature. After evaporation of the solution, the residue was triturated in refluxing ethanol for one hour. The solid was collected by filtration and dried. There was obtained 2.51 g as an off-white solid, $[\alpha]_D^{26°} = 25° \pm 1(H_2O)$.

EXAMPLE 25

Tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide Into a warm solution of 91 g of triethylamine sulfur trioxide complex and 91 g of 4A molecular sieves in dry N,N-dimethylacetamide was dissolved 14.9 g of N,N'-bis-[4-[4-O-(α-D-glucopyranosyl)-β-D-glucopyranosylthio]phenyl]octanediamide. The resulting solution was allowed to stand at 60°–65° C. in an oil bath, under argon, for 66 hours. The mixture was filtered and the filtrate poured into 3500 ml of acetone. After standing for one hour, the supernatant solution was decanted and the residual gum (tetradecatriethylammonium salt) was washed with three 150 ml portions of acetone. The gum was then dissolved in a solution composed of 19.7 g of anhydrous sodium acetate in 100 ml of water. This solution was added in a thin stream, with stirring, to 3500 ml of absolute ethanol, stirred for 20 minutes and then allowed to stand for 2 hours. The supernatant was siphoned from the solid which was then collected on a filter and washed repeatedly with absolute ethanol and finally with ether. Vacuum drying at 40° C. provided 33.6 g of the desired product as an amorphous powder.

To remove residual amounts of sodium sulfate the product was redissolved in 200 ml of water and mixed with 40 ml of 1 M barium acetate solution. The solution was centrifuged at 3000 rpm for 30 minutes and the cloudy supernatant was decanted and filtered through a 90S clarification filter, which in turn was washed with a small amount of water. The clear filtrate was passed through 400 g of activated Amberlite® CG-120 ion exchange resin (Na+ form), packed into a 60 mm. ID glass column. The sample was washed off the column with distilled water and fractions containing carbohydrate were pooled. The combined fractions were evaporated to 150 ml and the title compound was precipitated with 4 liters of hot ethanol. The solid was collected and dried in vacuo at 110° C. giving 23.9 g of yellow powder, $[\alpha]_D^{26°} = +17° \pm 1(1.1\%, H_2O)$.

EXAMPLES 26–35

Following the procedure of Example 25, the intermediates of Examples 15–24 are converted to the products of Examples 26–35 as given in Table III.

TABLE III

| Example | Intermediate (Example) | Product |
|---|---|---|
| 26 | 15 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]butanediamide |
| 27 | 16 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]pentanediamide |
| 28 | 17 | Tetradecasodium N,N'—bis[4-[2,3,6-tri-O—sulfo-4-O—(2,3,4,6-tetra-O—sulfo-α-D-glucopyranosyl)-β-D-glycopyranosylthio]phenyl]hexanediamide |
| 29 | 18 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]heptanediamide |
| 30 | 19 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]decanediamide |
| 31 | 20 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]propanediamide |
| 32 | 21 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]tetradecanediamide |
| 33 | 22 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]ethanediamide |
| 34 | 23 | Tetradecasodium N,N'—bis[4-[2,3,6-tri-O—sulfo-4-O—(2,3,4,6-tetra-O—sulfo-β-D-glucopyranosyl)-β-D-glucopyranosylthio]phenyl]pentanediamide |
| 35 | 24 | Tetradecasodium N,N'—bis[4-[2,3,6-tri-O—sulfo-4-O—(2,3,4,6-tetra-O—sulfo-α-D-glucopyranosyl)-β-D-glucopyranosylthio]phenyl]butanediamine |

EXAMPLE 36

Preparation of Compressed Tablet

| Ingredient | mg/Tablet |
|---|---|
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 37

Preparation of Compressed Tablet—Sustained Action

| Ingredient | mg/Tablet |
|---|---|
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement modulator plus aluminum sulfate yields aluminum complement modulator. Complement modulator content in aluminum lake ranges from 5–30%.

EXAMPLE 38

Preparation of Hard Shell Capsule

| Ingredient | mg/Capsule |
| --- | --- |
| Active Compound | 0.5-500 |
| Lactose, Spray Dried | qs |
| Magnesium Stearate | 1-10 |

EXAMPLE 39

Preparation of Oral Liquid (Syrup)

| Ingredient | % W/V |
| --- | --- |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 40

Preparation of Oral Liquid (Elixir)

| Ingredient | % W/V |
| --- | --- |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 41

Preparation of Oral Suspension (Syrup)

| Ingredient | % W/V |
| --- | --- |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 42

Preparation of Injectable Solution

| Ingredient | % W/V |
| --- | --- |
| Active Compound | 0.05-5 |
| Benzyl Alcohol N F | 0.9 |
| Water for Injection | 100.0 |

EXAMPLE 43

Preparation of Injectable Oil

| Ingredient | % W/V |
| --- | --- |
| Active Compound | 0.05-5 |
| Benzyl Alcohol | 1.5 |
| Sesame Oil qs ad | 100.0 |

EXAMPLE 44

Preparation of Intra-Articular Product

| Ingredient | Amount |
| --- | --- |
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 45

Preparation of Injectable Depo Suspension

| Ingredient | % W/V |
| --- | --- |
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N F | 0.9 |
| HCl to pH 6-8 | qs |
| Water for Injection qs ad | 100.0 |

EXAMPLE 46

Preparation of Dental Paste

| Ingredient | % W/V |
| --- | --- |
| Active Compound | 0.05-5 |
| Zinc Oxide | 15 |
| Polyethylene Glycol 4000 USP | 50 |
| Distilled Water qs | 100 |

EXAMPLE 47

Preparation of Dental Ointment

| Ingredient | % W/W |
| --- | --- |
| Active Compound | 0.05-5 |
| Petrolatum, White USP qs | 100 |

EXAMPLE 48

Preparation of Topical Ointment

| Ingredient | % W/W |
| --- | --- |
| Active Compound | 0.05-5 |
| Cholesterol | 3 |
| Stearyl Alcohol | 3 |
| White Wax | 8 |
| Petrolatum, White USP qs | 100 |

EXAMPLE 49

Preparation of Spray Lotion (Non-aerosol)

| Ingredient | % W/W |
| --- | --- |
| Active Compound | 0.05–5 |
| Isopropyl Myristate | 20 |
| Alcohol (Denatured) qs | 100 |

EXAMPLE 50

Preparation of Buccal Tablet

| Ingredient | g/Tablet |
| --- | --- |
| Active Ingredient | 0.00325 |
| 6 × Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg and may be compressed into buccal tablets in flat faced or any other tooling shape convenient for buccal administration.

EXAMPLE 51

Preparation of Dental Cream

| Ingredient | % W/W |
| --- | --- |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 52

Preparation of Topical Cream

| Ingredient | % W/W |
| --- | --- |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 53

Preparation of Lozenge

| Ingredient | g./Lozenge |
| --- | --- |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |

-continued

| Ingredient | g./Lozenge |
| --- | --- |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Cap 50 Test—Here, appropriate amounts of the test compound are added to a pool of guinea pig (or human) serum in vitro, after which the undiluted serum capillary tube assay of U.S. Pat. No. 3,876,376 is run. The concentration of compound inhibiting 50% is reported; and (iv) Guinea Pig Intraperitoneal Test (GPIP)—Guinea pigs weighing about 300 g are dosed intraperitoneally (i.p.) with 200 mg/kg of the test compound dissolved in saline and adjusted to pH 7-8. Approximately 0.4 ml blood samples, taken by orbital sinus puncture 2 hours and 6 hours after injections, are collected directly into centrifuge tubes; 5 ml blood samples, taken by decapitation 24 hours after injection, are collected directly into beakers. The samples are allowed to clot, centrifuged, and the resultant sera are assayed for complement activity using the capillary complement assay. Percent inhibition is calculated by comparison with simultaneous controls. The results of the GPIP appear in Table IV together with results of Test Code 026, 035, and Cap 50. Table IV shows that the principal compounds of the invention possess highly significant complement modulating activity in warm-blooded animals.

TABLE IV

| | in vitro Activity | | | | in vivo Activity Guinea Pig % Inhibition | | |
|---|---|---|---|---|---|---|---|
| | C1 026* | C-Late 035* | Guinea Pig | Human | Intraperitoneal Time (Hours) | | |
| Compound | Wells | Wells | Cap 50 | Cap 50 | 2 | 6 | 24 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]octanediamide | 9** | 1.5** | 153 | 180 | 87 | 71 | 44 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]butanediamide | 10.2 | 1.4 | 236 | 40 | 85 | 83 | 34 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]pentanediamide | 9.9 | 1.5 | 156 | 58 | 90 | 88 | 44 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]hexanediamide | 10.5 | 1.0 | 56 | 94 | 90 | 85 | 76 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]heptanediamide | 10.7 | 1.0 | 183 | 95 | 87 | 87 | 50 |
| Tetradecasodium N,N'-bis[4-[2,3,6-tri-O—sulfo-4-O—(2,3,4,6-tetra-O—sulfo-α-D-glucopyranosyl)-β-D-glucopyranosylthio]-phenyl]decanediamide | 5.0 | 0.8 | 121 | 394 | 88 | 87 | 75 |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]propanediamide | 9.9 | 1.6 | 158 | 84 | 90 | 90 | 47 |
| Tetradecasodium N,N'—bis[4-[2,3,6-tri-O—sulfo-4-O—(2,3,4,6-tetra-O—sulfo-β-D- | 12 | 2.0 | | | | | |

TABLE IV-continued

| | in vitro Activity | | | | in vivo Activity Guinea Pig % Inhibition Intraperitoneal Time (Hours) | | |
|---|---|---|---|---|---|---|---|
| Compound | Cl 026* Wells | C-Late 035* Wells | Guinea Pig Cap 50 | Human Cap 50 | 2 | 6 | 24 |
| glucopyranosyl)-β-D-glucopyranosylthio]-phenyl]pentanediamide | | | | | | | |
| Tetradecasodium N,N'—bis[4-[2,3,6-tri-O—sulfo-4-O—(2,3,4,6-tetra-O—sulfo-α-D-glucopyranosyl)-β-D-glucopyranosylthio]-phenyl]tetradecanediamide | 7 | 3.0 | | | | | |
| Tetradecasodium N,N'-bis[4-[2,3,6-tri-O—sulfo-4-O—(2,3,4,6-tetra-O—sulfo-α-D-glucopyranosyl)-β-D-glucopyranosylthio]-phenyl]ethanediamide | 9.5 | 1.2 | 213 | 124 | 90 | 90 | 80 |

*Tests identified by code herein.
**Activity in wells, a serial dilution assay; higher well number indicates higher activity. The serial dilutions are two-fold.

We claim:

1. A compound selected from those of the formula:

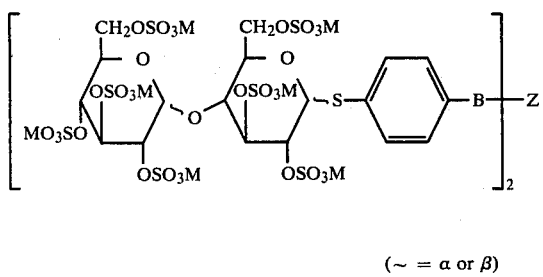

(∼ = α or β)

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$-$C_6$), piperidine, pyrazine, alkanolamine ($C_2$-$C_6$) and cycloalkylamine ($C_3$-$C_6$); B is selected from the group consisting of —NHCO—, —NHSO$_2$—, —NHCH$_2$— and —NH—; and Z is a straight or branched chain alkylidene group —(CH$_2$)$_m$—, where m is an integer 0–12, inclusive, with the proviso that when m is zero or one, B cannot be —NHSO$_2$—.

2. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide.

3. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]butanediamide.

4. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]pentanediamide.

5. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]hexanediamide.

6. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]heptanediamide.

7. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide.

8. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]propanediamide.

9. The compound according to claim 1, tetradecasodium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide.

10. A compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide.

11. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide.

12. The compound according to claim 1, tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine.

13. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide.

14. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamide.

15. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]pentanediamide.

16. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]hexanediamide.

17. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]heptanediamide.

18. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide.

19. The compound according to claim 1, tetradecatriethylammonium N,N'-[4-[2,3,6-tri-O-sulfo-4-O-

(2,3,4,6-tetra-O-sulfo-α-D-glucopyranosyl)-β-D-glucopyranosylthio]phenyl]propanediamide.

20. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide.

21. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide.

22. The compound according to claim 1, tetradecatriethylammonium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide.

23. The compound according to claim 1, tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine.

24. A compound selected from those of the formula:

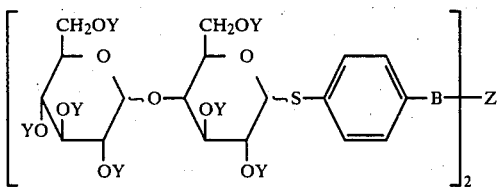

wherein Y is selected from the group consisting of H and COCH$_3$; B is selected from the group consisting of —NHCO—, —NHSO$_2$—, —NHCH$_2$— and —NH—; and Z is a straight or branched chain alkylidene group —(CH$_2$)$_m$—, where m is an integer 0–12, inclusive, with the proviso that when m is zero or one, B cannot be —NHSO$_2$—.

25. The compound according to claim 24, N,N'-bis[4-[4-O-(α-D-glucopyranosyl)-β-D-glucopyranosylthio]phenyl]octanediamide.

26. The compound according to claim 24, N,N'-bis[4-[4-O-(α-D-glucopyranosyl)-β-D-glucopyranosylthio]phenyl]butanediamide.

27. The compound according to claim 24, N,N'-bis[4-[4-O-(α-D-glucopyranosyl)-β-D-glucopyranosylthio]phenyl]pentanediamide.

28. The compound according to claim 24, N,N'-bis[4-[4-O-(α-D-glucopyranosyl)-β-D-glucopyranosylthio]phenyl]hexanediamide.

29. The compound according to claim 24, N,N'-bis[4-[4-O-(α-D-glucopyranosyl)-β-D-glucopyranosylthio]phenyl]heptanediamide.

30. The compound according to claim 24, N,N'-bis[4-[4-O-(α-D-glucopyranosyl)-β-D-glucopyranosylthio]phenyl]decanediamide.

31. The compound according to claim 24, N,N'-bis[4-[4-O-(α-D-glucopyranosyl)-β-D-glucopyranosylthio]phenyl]propanediamide.

32. The compound according to claim 24, N,N'-bis[4-[4-O-(α-D-glucopyranosyl)-β-D-glucopyranosylthio]phenyl]tetradecanediamide.

33. The compound according to claim 24, N,N'-bis[4-[4-O-(α-D-glucopyranosyl)-β-D-glucopyranosylthio]phenyl]ethanediamide.

34. The compound according to claim 24, N,N'-bis[4-[4-O-(β-D-glucopyranosyl)-β-D-glucopyranosylthio]phenyl]pentanediamide.

35. The compound according to claim 24, N,N'-bis[4-[4-O-(α-D-glucopyranosyl)-β-D-glucopyranosylthio]phenyl]butanediamine.

36. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]octanediamide.

37. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]butanediamide.

38. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]pentanediamide.

39. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]hexanediamide.

40. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]heptanediamide.

41. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]decanediamide.

42. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]propanediamide.

43. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]tetradecanediamide.

44. The compound according to claim 24, N,N'-bis[4-[2,3,6-tri-O-acetyl-4-O-(2,3,4,6-tetra-O-acetyl-α-D-glucopyranosyl)-β-D-glucopyranosylthio]phenyl]ethanediamide.

45. The compound according to claim 24, N,N'-bis[4-[2,3,6-tri-O-acetyl-4-O-(2,3,4,6-tetra-O-acetyl-β-D-glucopyranosyl)-β-D-glucopyranosylthio]phenyl]pentanediamide.

46. A method of modulating the complement system in a body fluid which comprises subjecting said body fluid to the action of an effective complement modulating amount of a pharmaceutically acceptable compound selected from those of the formula of claim 1.

47. The method according to claim 46, wherein the body fluid is blood serum.

48. A method of modulating the complement system in a warm-blooded animal which comprises administering to said warm-blooded animal an effective complement modulating amount of a pharmaceutically acceptable compound selected from those of the formula of claim 1.

49. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide.

50. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]butanediamide.

51. The method according to claim 46 or 48, wherein the compound is tetradecasodium N,N'-bis[4-[2,3,6-tri- O-sulfo-4-O-(2,3,4,6-tetra-O-sulfo-α-D-glucopyranosyl)-β-D-glucopyranosylthio]phenyl]pentanediamide.

52. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]hexanediamide.

53. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]heptanediamide.

54. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide.

55. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]propanediamide.

56. The method according to claim 46 or 48, wherein the compound is tetradecasodium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide.

57. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide.

58. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide.

59. The method according to claim 46 or 48, wherein the compound is tetradecasodium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine.

60. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]octanediamide.

61. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamide.

62. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]pentanediamide.

63. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]hexanediamide.

64. The method according to claim 46 or 48, wherein the compound is tetradecatriethylammonium N,N'-bis[4-[2,3,6-tri-O-sulfo-4-O-(2,3,4-tetra-O-sulfo-α-D-glucopyranosyl)-β-D-glucopyranosylthio]phenyl]heptanediamide.

65. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]decanediamide.

66. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]propanediamide.

67. The method according to claim 46 or 48, wherein the compound is tetradecatriethylammonium N,N'-bis[4-[2,3,6-tri-O-sulfo-4-O-(2,3,4,6-tetra-O-sulfo-β-D-glucopyranosyl)-β-D-glucopyranosylthio]phenyl]pentanediamide.

68. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]tetradecanediamide.

69. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]ethanediamide.

70. The method according to claim 46 or 48, wherein the compound is tetradecatriethylammonium N,N'-bis[4-[2,3,6-tri-O-sulfo-4-O-(2,3,4,6-tetra-O-sulfo-α-D-glucopyranosyl)-β-D-glucopyranosylthio]phenyl]butanediamine.

71. The method according to claim 48, wherein the compound is administered internally.

72. The method according to claim 48, wherein the compound is administered topically.

73. The method according to claim 48, wherein the compound is administered periodontally in the oral cavity.

74. The method according to claim 48, wherein the compound is administered intra-articularly.

75. The method according to claim 48, wherein the compound is administered parenterally.

76. A process for the preparation of compounds of the formula:

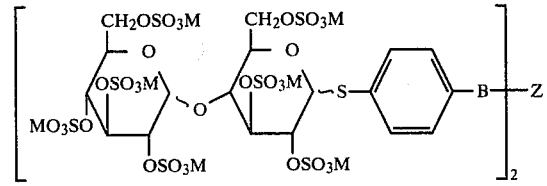

(∼ = α or β)

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); B is selected from the group consisting of —NHCO—, —NHSO$_2$—, —NHCH$_2$—, and —NH—; and Z is a straight or branched chain alkylidene group —(CH$_2$)$_m$—, where m is an integer 0–12, inclusive, with the proviso that when m is zero or one, B cannot be —NHSO$_2$—; which comprises reacting 4-aminothiophenol in dimethoxyethane and sodium hydride in oil with a solution of acetobromo-α-D-maltose or cellobiose in dimethoxyethane, under an inert atmosphere, for 18 hours, subjecting the mother liquor to dry column chromatography on silica gel using the solvent system ethyl acetate:hexane (1:1) giving 4-aminophenyl 2,3,6-tri-O-acetyl-4-O-(2,3,4,6-tetra-O-acetyl-α(or β)-D-glucopyranosyl)-1-thio-α(or β)-D-glucopyranoside; then reacting with an appropriate acid chloride of the formula X—$(CH_2)_m$—X, where X is COCl or $SO_2Cl$ and m is an integer 0–12 (with the proviso that when m is zero or one X cannot be $SO_2Cl$), in dry pyridine:acetonitrile (1:1) under an inert atmosphere for 18–36 hours, extracting from a suitable organic solvent, giving a compound of the formula:

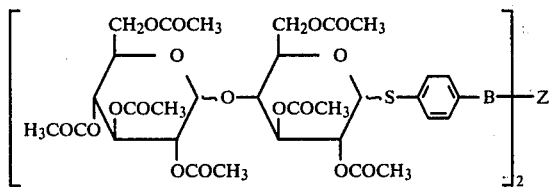

where B and Z are as hereinabove defined, treating this acetylated derivative in ammonia saturated methanol at 0° C., or sodium in methanol, for 18–24 hours; extracting from absolute ethanol, giving the corresponding deacetylated derivative of the formula:

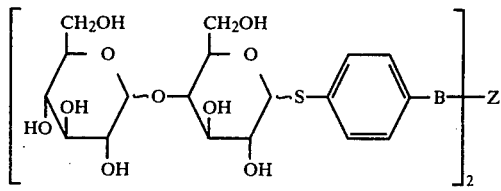

where B and Z are as hereinabove defined, then converting to the tetradecatriethylammonium sulfate derivatives of the formula:

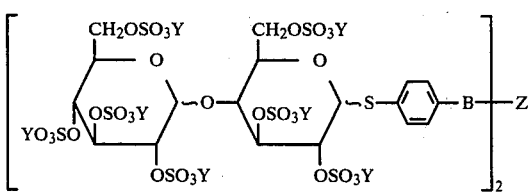

where B and Z are as hereinabove defined and Y is $NH^+(C_2H_5)_3$, by treating with triethylamine-sulfur trioxide complex in N,N-dimethylacetamide, under an inert atmosphere at 60°–65° C., for 66 hours; reacting with a cation-containing compound wherein the salt forming moiety is selected from the group consisting of alkali metal, alkaline earth metal, aluminum, ammonia and substituted ammonia selected from the group consisting of piperidine, pyrazine, alkanolamine ($C_2$–$C_6$) and cycloalkylamine ($C_3$–$C_6$), and thereafter precipitating in ethanol, giving the desired products.

* * * * *

UNITED STATES PATENT OFFICE
CERTIFICATE OF CORRECTION

Patent No. 4,399,126  Dated  August 16, 1983

Inventor(s) ROBERT E. SCHAUB, JANIS UPESLACIS & SEYMOUR BERNSTEIN

It is certified that error appears in the above-identified patent and that said Letters Patent are hereby corrected as shown below:

Column 22, Claim 19, line 67: "N,N'-[4-[2,3,6-tri-O-sulfo-4-O-" should read -- N,N'-bis[4-[2,3,6-tri-O-sulfo-4-O- --;

Column 23, Claim 24, line 31: after formula, insert -- (∼ = α or β) --;

Column 25, Claim 64, line 66: "sulfo-4-O-(2,3,4-tetra-O-sulfo" should read -- sulfo-4-O-(2,3,4,6-tetra-O-sulfo- --;

Columns 27 & 28, Claim 76: after each formula, insert -- (∼ = α or β) -- .

Signed and Sealed this

First Day of May 1984

[SEAL]

Attest:

GERALD J. MOSSINGHOFF

Attesting Officer

Commissioner of Patents and Trademarks